US00PP26718P2

(12) United States Plant Patent
Nishikawa

(10) Patent No.: US PP26,718 P2
(45) Date of Patent: May 10, 2016

(54) ***CALENDULA* PLANT NAMED '20124-R'**

(50) Latin Name: *Calendula officinalis*
Varietal Denomination: 20124-R

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 100 days.

(21) Appl. No.: 14/120,527

(22) Filed: May 29, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Penny J. Aguirre

(57) ABSTRACT

A new cultivar of *Calendula* plant, '20124-R', that is characterized by its strong, compact, creeping plant habit, its double flowers that are yellow in color, its long flowering time; blooming for 9 months from spring into winter in Noordwijkerhout, The Netherlands, its very high tolerance to powdery mildew, and its very high tolerance to heat and cold, withstanding temperatures below −20° C. in the winter and in its ability to be readily propagated by stem cuttings.

2 Drawing Sheets

Botanical classification: *Calendula officinalis*.
Variety denomination: '20124-R'.

CROSS REFERENCE TO RELATED APPLICATIONS

This application is co-pending with U.S. Plant Patent Applications filed for plants derived from the same breeding program that are entitled *Calendula* Plant Named '20124-30D' (U.S. Plant patent application Ser. No. 14/120,524) and *Calendula* Plant Named '20123-5D' (U.S. Plant patent application Ser. No. 14/120,525).

BACKGROUND OF THE INVENTION

The present invention relates to a new and distinct cultivar of *Calendula* plant, botanically known as *Calendula officinalis* '20124-R', and will be referred to hereinafter by its cultivar name, '20124-R'. The new cultivar of *Calendula* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of vegetatively propagated *Calendula* plants with low-growing and well-spreading growth habits combined with long flowering periods and a unique range of flower colors.

'20124-R' was selected in the Inventor's trial garden in 2012 as a single unique plant from amongst the seedlings derived from self-crossing an unnamed plant from the Inventor's breeding program, ref. code 20122-20D, in 2012.

Asexual propagation of the new cultivar was first accomplished by softwood stem cuttings in summer of 2012 by the Inventor in Katsuta-Gun, Okayama-Pref., Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish '20124-R' as a unique cultivar of *Calendula*.

1. '20124-R' exhibits a strong, compact, creeping plant habit.
2. '20124-R' exhibits double flowers that are yellow in color.
3. '20124-R' exhibits a long flowering time; blooming for 9 months from spring into winter in Noordwijkerhout, The Netherlands.
4. '20124-R' exhibits very high tolerance to powdery mildew.
5. '20124-R' exhibits very high tolerance to heat and cold, withstanding temperatures below −20° C. in the winter.
6. '20124-R' is readily propagated by stem cuttings.

'20124-R' can best be compared to plants of the *Calendula* seed strain 'Alice'. 'Alice' differs from '20124-R' in having flowers that are larger in size, in having a shorter four month long blooming period, in being poorly branched, in being susceptible to powdery mildew, heat, and cold, and in being propagated by seed. '20124-R' can also be compared to the co-pending *Calendula* cultivars '2012-3-5D' and '20124-30D'. '20123-5D' differs from '20124-R' in having flowers that are a blend of pale yellow to light peach in color. '20124-30D' differs from '20124-R' in having flowers that bright yellow-orange in color. There are no cultivars of *Calendula officinalis* that are vegetatively propagated known to the Inventor. The Inventor has no records on the characteristics of the parent plant.

BRIEF DESCRIPTION OF THE DRAWINGS

The accompanying colored photographs illustrate the overall appearance and distinct characteristics of the new *Calendula*. The plant in the photograph is four months in age as grown outdoors in a 20-cm container in Noordwijkerhout, The Netherlands.

The photograph in FIG. 1 provides a side view of the plant habit of '20124-R' in bloom.

Figure 1:
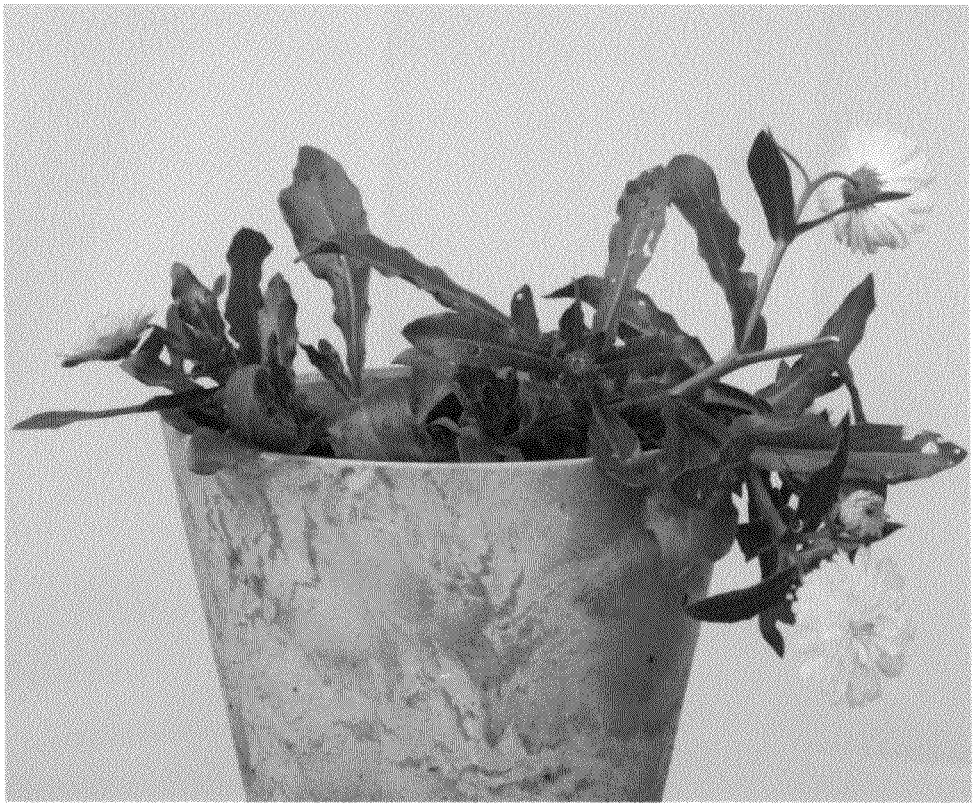
Figure 2:
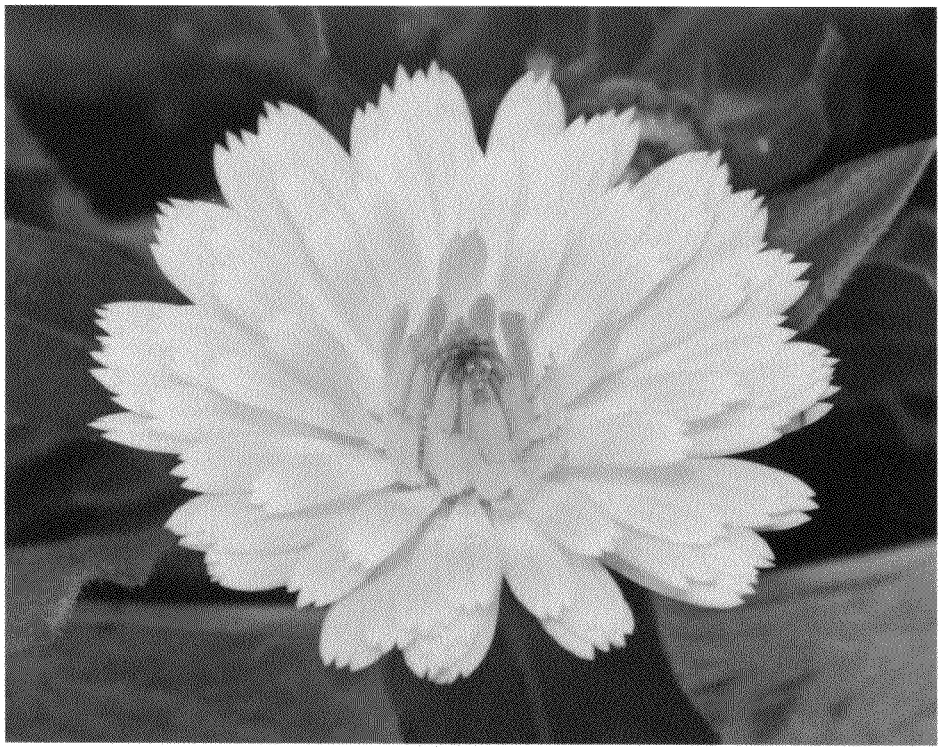

The photograph in FIG. 2 provides a close-up view of a flower of '20124-R'.

Figure 3:
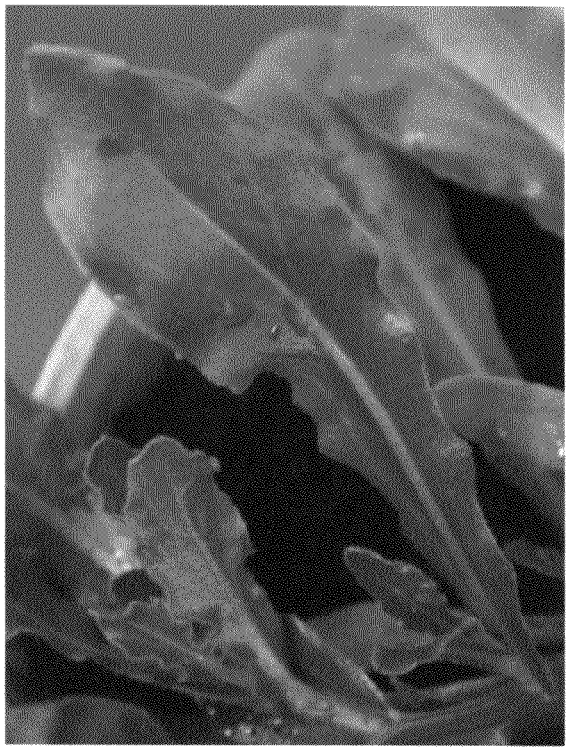

The photograph in FIG. 3 provides a close-up view of the foliage of '20124-R'.

The colors in the photographs may differ slightly from the color values cited in the detailed botanical description, which accurately describe the colors of the new *Calendula*.

DETAILED BOTANICAL DESCRIPTION

The following is a detailed description of four month-old plants of the new cultivar as grown outdoors in 20-cm containers in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—An average of nine months from spring into winter in Noordwijkerhout, The Netherlands.

*Plant type.*—Herbaceous perennial.

*Plant habit.*—Compact and creeping plant habit.

*Height and spread.*—An average of 15.5 cm in height and 32.8 cm in diameter.

*Cold hardiness.*—Observed to be hardy to U.S.D.A. Zone 7.

*Diseases.*—Has been shown a high tolerance of powdery mildew.

*Root description.*—Fine and fibrous roots.

*Propagation.*—Softwood stem cuttings.

*Growth rate.*—Vigorous.

Stem description:

*Shape.*—Rounded.

*Stem color.*—143A, upper surface strongly suffused with 200B.

*Stem size.*—An average of 10 cm in length and 5 mm in diameter.

*Stem strength.*—Strong.

*Stem aspect.*—Lateral stems grow at an average angle of 70° to the main stems.

*Stem surface.*—Moderately glossy, moderately covered with very short soft hairs, an average of 0.5 mm in length and NN155D in color.

*Internode length.*—Average of 2.1 cm in length.

*Branching.*—Main stems grow from base with an average of six lateral stems per main stem.

Foliage description:

*Leaf shape.*—Oblanceolate to narrow oblong.

*Leaf division.*—Simple.

*Leaf base.*—Truncate, decurrent.

*Leaf apex.*—Obtuse to broadly acute.

*Leaf venation.*—Pinnate, color: upper and lower surface; 144A.

*Leaf margins.*—Sinuate.

*Leaf attachment.*—Decurrent.

*Leaf arrangement.*—Alternate.

*Leaf size.*—Average of 12.1 cm in length and 3.2 cm in width.

*Leaf color.*—Young upper surface; 139A, young lower surface; N137B, mature upper surface; N137A to N137B, mature lower surface; 146B and 147B.

*Leaf surface.*—Upper and lower surfaces are moderately covered with very short strigose hairs 0.03 cm in length and NN155D in color, upper surface is glossy and rough to the touch, lower surface is dull and rough to the touch.

*Leaf fragrance.*—None.

*Petioles.*—Absent.

Inflorescence description:

*Inflorescence type.*—Terminal capitulum consisting of ray florets only.

*Inflorescence number.*—An average of 7 per plant.

*Flower number.*—Average of 1 per lateral stem.

*Flower fragrance.*—No fragrance.

*Flower aspect.*—Straight on top of stem.

*Flower longevity.*—A few weeks.

*Flower size.*—Average of 1.4 cm in height and 5.5 cm in diameter.

*Flower buds.*—Average of 2 per lateral stem, flattened globular in shape, average of 8 mm in length and 1.1 cm in diameter, color; 137C to 137D, top is 151B to 151D.

*Receptacle.*—Flattened globular in shape, 0.3 cm in height and 0.5 cm in diameter, 145D in color.

*Peduncle.*—Average of 2.1 cm in length and 2 mm in diameter, terminal peduncle is straight on top of stem, other peduncles at an average angle of 30° to the stem, moderate strength, color is 143A, moderately covered with short soft hairs, average of 0.5 mm in length and NN155D in color.

*Involucral bracts* (*phyllaries*).—Average of 20 per inflorescence, arranged in one row, lanceolate in shape, narrowly acute apex, cuneate base, margin entire, 9 mm in length, 1.75 mm in width, upper surface is glabrous, lower surface is densely covered with very short pubescence, average length is 0.5 mm and 157D in color, color: upper surface 137B, lower surface 137A.

Ray florets:

*Number.*—Average of 125.

*Arrangement.*—Rotate, 6 whorls.

*Shape.*—Oblanceolate.

*Aspect.*—Slightly upright at the base, held in an average angle of 30°, whole ray floret near horizontal.

*Size.*—Average of 2.4 cm in length and 0.5 cm in width.

*Ray floret apex.*—Praemorse.

*Ray floret base.*—Narrow cuneate.

*Ray floret margins.*—Entire.

*Ray floret surface.*—Both sides glabrous, dull, and velvety.

*Ray floret color.*—Opening upper surface a blend between 23A and N25C, base is 9A, opening lower surface; 17B to 17C, base is 9A, when fully open upper surface; 17B to 17C, base is 6A, when fully open lower surface; 9A, tip is 12A, fades to 12A with base 5A on the upper surface and fades to 9A on the lower surface.

*Disk florets.*—Absent.

Reproductive organs:

*Gynoecium.*—1 pistil per ray floret, 5 mm in length, stigma unequal decurrent and 13A in color, style is 2.5 mm in length and 5C in color, ovary 150D in color.

*Androecium.*—No stamen present.

*Fruit and seed.*—No fruits or seeds observed to date.

It is claimed:

1. A new and distinct variety of *Calendula* plant named '20124-R' as described and illustrated herein.

* * * * *